United States Patent

Begemann et al.

[11] Patent Number: 6,052,621
[45] Date of Patent: *Apr. 18, 2000

[54] SYSTEM AND METHOD FOR INDUCING TACHYCARDIA

[75] Inventors: Malcolm J. S. Begemann, Velp; Karel den Dulk; Henny M. Leerssen, both of Maastricht; Volkert A. Zeijlemaker, Landgraaf, all of Netherlands

[73] Assignee: Vitatron Medical B.V., Dieren, Netherlands

[*] Notice: This patent is subject to a terminal disclaimer.

[21] Appl. No.: 09/014,378

[22] Filed: Jan. 27, 1998

[51] Int. Cl.⁷ ........................................ A61N 1/39
[52] U.S. Cl. .................................. 607/28; 607/2
[58] Field of Search .................. 607/4, 5, 6, 7, 607/8, 9, 25, 28, 2

[56] References Cited

U.S. PATENT DOCUMENTS

| | | | |
|---|---|---|---|
| 4,343,312 | 8/1982 | Cals et al. | 128/419 PG |
| 4,390,021 | 6/1983 | Spurrell et al. | 128/419 PG |
| 4,401,120 | 8/1983 | Hartlaub et al. | 128/419 PG |
| 4,550,370 | 10/1985 | Baker | 364/413 |
| 4,556,063 | 12/1985 | Thompson et al. | 128/419 PT |
| 4,593,695 | 6/1986 | Wittkampf | 128/419 PG |
| 5,129,392 | 7/1992 | Bardy et al. | 128/419 D |
| 5,156,149 | 10/1992 | Hudrlik | 128/419 PG |
| 5,233,985 | 8/1993 | Hudrlik | 607/27 |

*Primary Examiner*—Scott M. Getzow
*Attorney, Agent, or Firm*—Michael J. Jaro; Harold Patton

[57] ABSTRACT

A system and method are provided for inducing ventricular tachycardia in a patient to enable testing to determine the optimum parameters for anti-tachycardia stimulation. The implantable device provides for overdrive pacing of the heart for a short sequence, followed by delivery of a series of pulse pairs. Each pulse pair has a first stimulus pulse delivered at the same or similar overdrive rate, and an inducing pulse which is delivered in timed relation to the evoked T-wave, preferably during the falling edge portion of the T-wave. In this way, each cycle the inducing pulse is timed for efficaciously inducing tachycardia. The timing of the inducing pulse is enhanced by near field sensing of the T-wave at about the location where the pulses are delivered, preferably using bipolar sensing and/or sense circuitry designed to recover the signal with an optimum time response.

28 Claims, 4 Drawing Sheets

SYSTEM AND METHOD FOR INDUCING TACHYCARDIA

FIELD OF THE INVENTION

This invention relates to cardiac stimulus systems which have a cardioversion capacity and, more particularly, to such cardiac systems which have the further capability of inducing ventricular tachycardia or fibrillation in a patient so that cardioversion parameters can be tested and set.

BACKGROUND OF THE INVENTION

The treatment of abnormally and physiologically dangerous high cardiac rate conditions, i.e., tachycardia and fibrillation, has become very important, and is the subject of considerable development. For example, modern implantable cardiac pacemakers can be provided with an anti-tachycardia feature, whereby the implantable device senses the occurrence of tachycardia, and responds by delivering one or more stimuli in a pattern designed to eliminate the dangerous high rate. Likewise, implantable defibrillators are designed to determine the occurrence of fibrillation, and to respond automatically with one or more defibrillation pulses. In this specification, the reference to abnormally high rates, or high rate conditions, incorporates the range of abnormal conditions, through all tachycardia rates up to and including fibrillation. Thus, the term tachycardia as used herein embraces the range of abnormally high rates, up to and including fibrillation. The treatment of such conditions, i.e., anti-tachycardia treatment or defibrillation, is referred to generally as cardioversion. The devices which can provide such cardioversion treatment can be specifically designed for a given treatment, i.e., defibrillators, or can be devices which combine pacing functions and one or more types of cardioversion treatment.

When implanting such an implantable device which provides for cardioversion, it is necessary to test the device operationally, and set the stimulus parameters so as to ensure reliable treatment. Thus, for a pacemaker having a feature of terminating ventricular tachycardia (VT), it is important to test at time of implant to determine that the prescribed pattern of anti-tachycardia stimulus pulses is delivered with the optimal parameters to control and terminate the VT for the patient receiving the implant. In order to carry out such a test, it is necessary to first induce the VT (or other high rate condition), and then set the anti-tachycardia stimulus parameters, e.g., timing and energy, for optimal termination of the VT. The aim of this invention is to provide the device with an improved and more reliable capability of inducing such a high rate abnormal condition, for test purposes.

It is known that tachycardia or fibrillation can be stopped, or terminated by delivery of stimulus pulses which interfere with the re-entry loop mechanism. Thus, in terminating such a non-physiological condition, a stimulus pulse is delivered shortly after the cardiac refractory period, and before the next expected spontaneous beat. In U.S. Pat. No. 4,390,021, there is disclosed the standard technique of delivering a pair of pulses, each timed with respect to the preceding QRS so as to fall within a "region of susceptibility," in order to break up the tachycardia. The system of the disclosure relies on searching to find the timing which results in break up of tachycardia, i.e., to find the "region of susceptibility." It is mentioned that a similar technique can be used to induce tachycardia, but no specifics are mentioned with regard to the required timing. It is noted that the timing for inducing tachycardia is not necessarily the same, relative to the QRS, as for breaking up tachycardia.

U.S. Pat. No. 4,593,695 discloses a successful technique for terminating VT which involves overdriving the ventricle with an early stimulus pulse, detecting the occurrence of the repolarization which is manifested by the T-wave, and then delivering a stimulus which is intended to break up the tachycardia. Since the T-wave is produced by cardiac cell repolarization and thus roughly indicates the end of the refractory period, it is necessary to wait until the T-wave detection in order to deliver a stimulus which can have an effect. Successive such early pulses can be delivered, as necessary to terminate the tachycardia condition. However, this reference gives no guidance concerning inducing tachycardia.

U.S. Pat. No. 5,129,392 is specifically directed to a technique of inducing fibrillation by delivery of a high voltage pulse following the refractory period of the heart chamber. The refractory period is disclosed to be determined by getting an average of the stimulus-T interval and delivering the high voltage pulse at a time based on this average and referenced to a preceding pacing pulse or spontaneous QRS. However, this technique has only about a 60% success rate, which means that often the delivery of a high energy pulse must be repeated. This produces substantial patient discomfort, and causes battery drain and consequent reduction of device longevity. Further, it is our observation that the timing with respect to the T-wave is critical, and accordingly it is desirable to do more than simply deliver an inducing pulse after the some predetermined interval following the QRS or the T-wave.

For an implantable device having an anti-tachycardia feature, it is desirable to be able to induce tachycardia using the vastly lower energy pacing pulses. This is the case whether the device is a pacemaker, or whether it incorporates cardioverting capacity, as with a combined pacemaker-cardioverter-defibrillator ("PCD"). In any case, it is highly desirable to provide the capability of inducing tachycardia by using only pacing-level pulses, to optimize patient comfort and save energy. This means that the tachy-inducing pulses are delivered as a series of smaller energy pulses. Since QT interval varies with rate, the delivery of the first inducing pulse likely has an effect on the following QT interval. The result of delivering a series of pulses is that each cycle the refractory interval may be slightly different, such that use of a fixed interval following the pacing stimulus or sensed QRS is relatively unlikely to be efficient in finding the proper time to induce VT. Accordingly, it is important to be able to determine on a cycle-to-cycle basis the best time to deliver the inducing pulse (or pulse pair). The solution provided by this invention is to look for the occurrence of a T-waves following respective QRS signals which have been evoked by a series of pacing pulses; and to deliver one or more inducing pulses in closely timed relation to a specific portion of each sensed T-wave.

SUMMARY OF THE INVENTION

It is a primary object of this invention to provide an implantable cardiac stimulating device which includes a feature for breaking up a sensed tachycardia, and in particular ventricular tachycardia, where the device also has the capability of inducing such a tachycardia with low energy pacing pulses, so as to enable accurate adjustment of the stimulus protocol for treating the tachycardia. The object of providing a tachycardia-inducing capability is achieved by accurate sensing of a predetermined portion or feature of the T-wave, and delivery of an inducing stimulus pulse to the patient's ventricle directly upon sensing of the T-wave portion. Preferably a series of pacing pulses is delivered at an overdrive rate, with a tachycardia inducing pulse delivered upon sensing of each T-wave which follows an evoked QRS. If an early QRS is sensed before delivery of a next scheduled overdrive pacing pulse, the inducing routine stops and looks for confirmation of tachycardia; if the entire series of pairs of pacing-level stimulus and inducing pulses is delivered, the device then looks for tachycardia, and if no tachycardia is confirmed, the inducing protocol can be repeated.

In the practice of this invention, it is important to deliver each inducing pulse while the T-wave is still on its negative, or downward slope, as measured in or close to the area of heart tissue where the pulses are delivered. Consequently, the system of this invention preferably includes a sensing electrode configuration and sensing circuitry for optimizing near field sensing.

BRIEF DESCRIPTION OF THE DRAWINGS

FIG. 4(*b*) is a block diagram illustrating the use of DSP sensing of a bipolar signal for obtaining the T-wave.

DESCRIPTION OF THE PREFERRED EMBODIMENTS

Figure 1A:
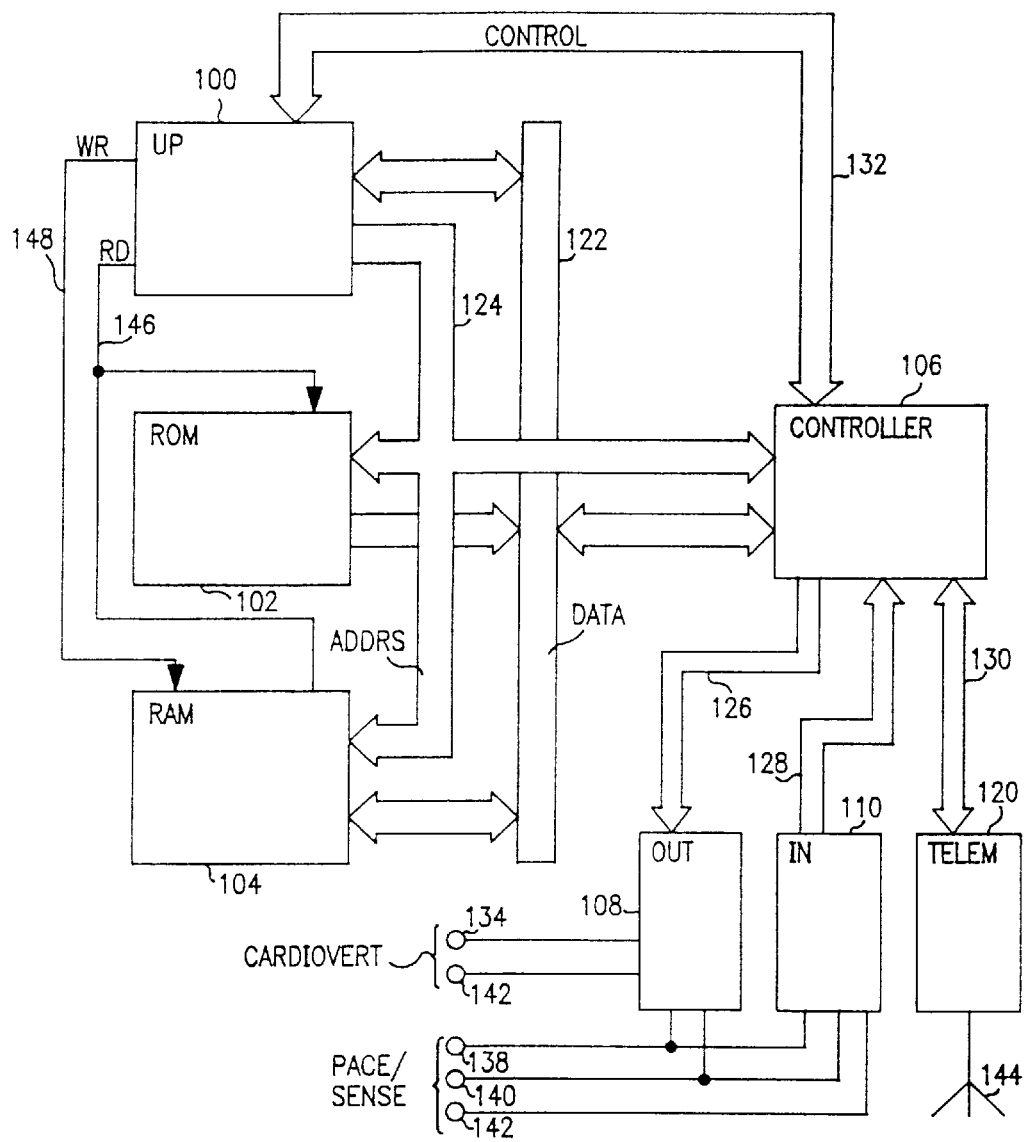
FIG. 1 is a functional block diagram of an implantable device representative of the devices in which the present invention is embodied.
FIG. 1B is an illustration of a lead having a tip electrode and a ring electrode for pacing and sensing, and a larger electrode for use in delivering cardioverting pulses.

FIG. 1 is a functional block diagram of an implantable pacemaker of the type in which the present invention may be practiced. The disclosed embodiment takes the form of a microprocessor controlled device. However, it is believed that the invention might usefully be practiced in other types of devices, including those employing dedicated digital circuitry, and perhaps even in devices comprised primarily of analog timing and control circuitry. As such, FIG. 1 should be considered exemplary, rather than limiting with regard to the scope of applications of the present invention. While the invention is disclosed as embodied in a pacemaker, it is equally applicable to incorporation in a cardioverter, or combined cardioverter pacemaker, or even cardioverter defibrillator pacemaker. While the following discussion of FIG. 1 assumes a single chamber ventricular pacing system, it is to be understood that the invention is applicable to dual chamber systems.

The primary elements of the apparatus illustrated in FIG. 1 are microprocessor 100, read only memory 102, random access memory 104, a digital controller 106, input and output amplifiers 110 and 108 respectively, and a telemetry/programming unit 120.

Read only memory 102 stores the basic programming for the device, including the primary instructions set defining the computations performed to derive the various timing intervals performed by the device. Random access memory 104 serves to store the values of variable control parameters, such as programmed pacing rate, programmed cardioversion and defibrillation intervals, pulse widths, pulse amplitudes, and so forth, which are programmed into the device by the physician. Random access memory also stores derived values, such as the interval defining the timing window for sensing T-waves, as discussed in connection with FIG. 2C. Reading from random access memory 104 and read only memory 102 is controlled by RD-line 146. Writing to random access memory 104 is controlled by WR-Line 148. In response to a signal on RD-Line 146, the contents of random access memory 104 or read only memory 102 designated by the then present information on address bus 124 are placed on data bus 122. Similarly, in response to a signal on WR-line 148, information on data bus 122 is written into random access memory 104 at the address specified by the information on address bus 124.

Figure 1B:
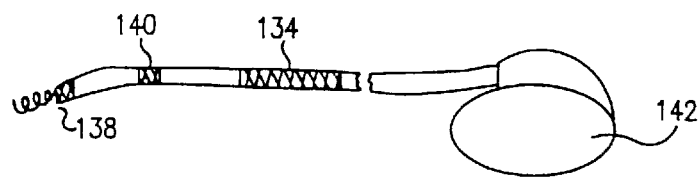

Controller 106 performs all of the basic timing and control functions of the device. Controller 106 includes at least one programmable timing counter, initiated on ventricular contractions, paced or sensed, for timing out intervals thereafter. This timing counter is used to define the escape intervals for overdrive pacing, and the delay interval (if one is used) for timing the triggering of an inducing pulse following a sensed T-wave. It is also anticipated that the controller 106 would also perform the basic timing functions of the pacing, and tachycardia detection routines performed by the device, in accordance with well known techniques. Controller 106 also triggers output pulses from output stage 108 as discussed below, and it generates interrupts on control bus 132 for cyclically waking microprocessor 100 from its sleep state to allow it to perform the required functions. Output circuit 108 is coupled to electrodes 138 and 140 which are employed both for delivery of pacing pulses and for sensing of cardiac signals. Electrode 138 is typically located on the distal tip end of an endocardial lead and is typically placed in the apex of the right ventricle; for atrial mode pacing, of course, it is placed in the patient's atrium. Electrode 140 is preferably a ring electrode positioned at most a few nmm from the tip electrode, for near field sensing. Electrode 142 represents the pacemaker housing, which may be used as the indifferent electrode for selected unipolar pacing and/or sensing operations, as discussed below. Output circuit 108 is controlled by controller 106 through bus 126 to determine the time, amplitude and pulse width of the pulse to be delivered and to determine which electrode pair will be employed to delivery the pulse. Output stage 108 also is used for delivery of the tachycardia-inducing pulses across electrodes 138, 140. In a PCD-type device, it may also be used for delivery of cardioverting pulses between electrodes 134 and can 142. Electrodes 134, 138 and 140 may suitably be provided by a lead such as shown in FIG. 1B, as provided by Medtronic lead Model 6932 (passive fixation) or Model 6936 (active fixation).

Sensing of QRS and T-waves is done by input amplifier circuitry 110, which receives sensed signals from electrodes 138, 140, and/or 142. Signals indicating the occurrences of natural ventricular contractions, and paced ventricular contractions as well as T-waves, are provided to the controller 106 via bus 128. Controller 106 passes data indicative of the occurrence of such ventricular signals to microprocessor 100 via control bus 132, for performance of all necessary calculations, and in particular for timing of the delivery of tachy-inducing pulses in the manner discussed below.

External control of the implanted device is accomplished via telemetry/control block 120, which allows communication between the implanted device and an external programmer, (not shown). Radio communication is typically employed via antenna 124. Appropriate telemetry/programming systems are disclosed in U.S. Pat. No. 4,401, 120, issued to Hartlaub et al., U.S. Pat. No. 4,556,063, issued to Thompson et al., and U.S. Pat. No. 4,550,370, issued to Baker, all of which are incorporated herein by reference in their entireties. However, any conventional telemetry/programming circuitry is believed workable in the context of the present invention. Information entering the pacemaker from the programmer is passed to controller 106 via bus 130. Similarly, information from the pacemaker is provided to the telemetry block 120 via bus 130, for transmission to the external programmer.

Figure 2A:
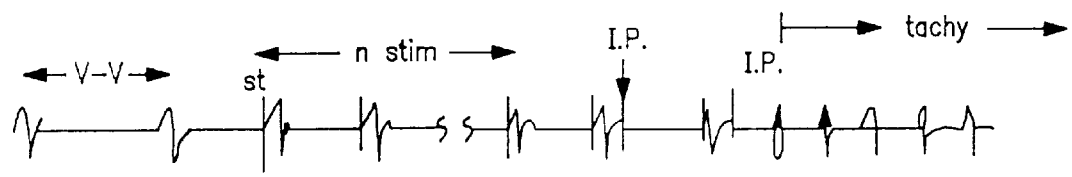
FIG. 2A is a timing diagram illustrating the sequence of overdrive pacing pulses and the timing of inducing pulses in accordance with this invention.

Referring now to FIG. 2A, there is shown a timing diagram illustrating the manner of delivering inducing pulses for inducing tachycardia in accord with this invention. The timing diagram illustrates delivering pulses to the ventricle for inducing VT, but it is to be understood that the invention is also applicable to inducing atrial tachycardia.

Figure 2B:
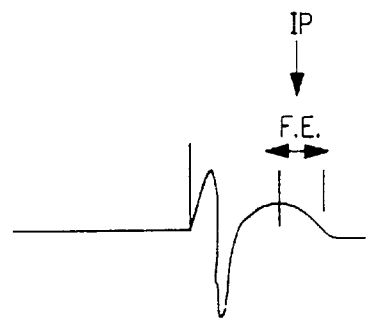
FIG. 2B is a timing diagram illustrating the preferred region of the T-wave which is sensed in order to best determine the timing of an tachycardia-inducing pulse in accordance with this invention.

Starting at the left of the timing diagram of FIG. 2A, there is shown a natural sinus beat existing in the patient, providing a V–V__int which is measured by the pacemaker or other implantable device. Following measurement of the V–V__int, a series of n stimulus pulses are delivered at a rate which is greater than the natural rate, i.e., the escape interval is shorter than the V–V__int. After delivering n such pulses, where n may be only one or two, or a greater number, a next pacing pulse is delivered at the same escape interval; following this an inducing pulse (designated IP) is delivered, preferably during the falling edge of the T-wave. As seen in FIG. 2B, the falling edge of the T-wave is defined as the downward slope following the maximum (peak) value of the T-wave. The inducing pulse can be delivered immediately, upon detection of the negative-going falling edge, or it can be delivered after timeout of a small time delay following the peak, where the delay is calculated to time out during the falling edge portion of the T-wave. As illustrated in FIG. 2A, two such inducing pulses are delivered, following which tachycardia occurs.

Figure 2C:
FIG. 2C is a timing diagram illustrating the use of a sensing window for sensing the T-wave signal in accordance with this invention.

Referring to FIG. 2C, there is shown a timing diagram illustrating a time window W, which is used to time the operation of a T-wave sense amplifier in a manner such as disclosed in U.S. Pat. No. 4,593,695, incorporated herein by reference. The timing window is adjusted after each detected T-wave, such that it tracks the expected time of the T-wave following a delivered stimulus, thereby enabling the sensing amplifier to look for the T-wave falling edge during a specific limited interval each cycle.

Figure 3:
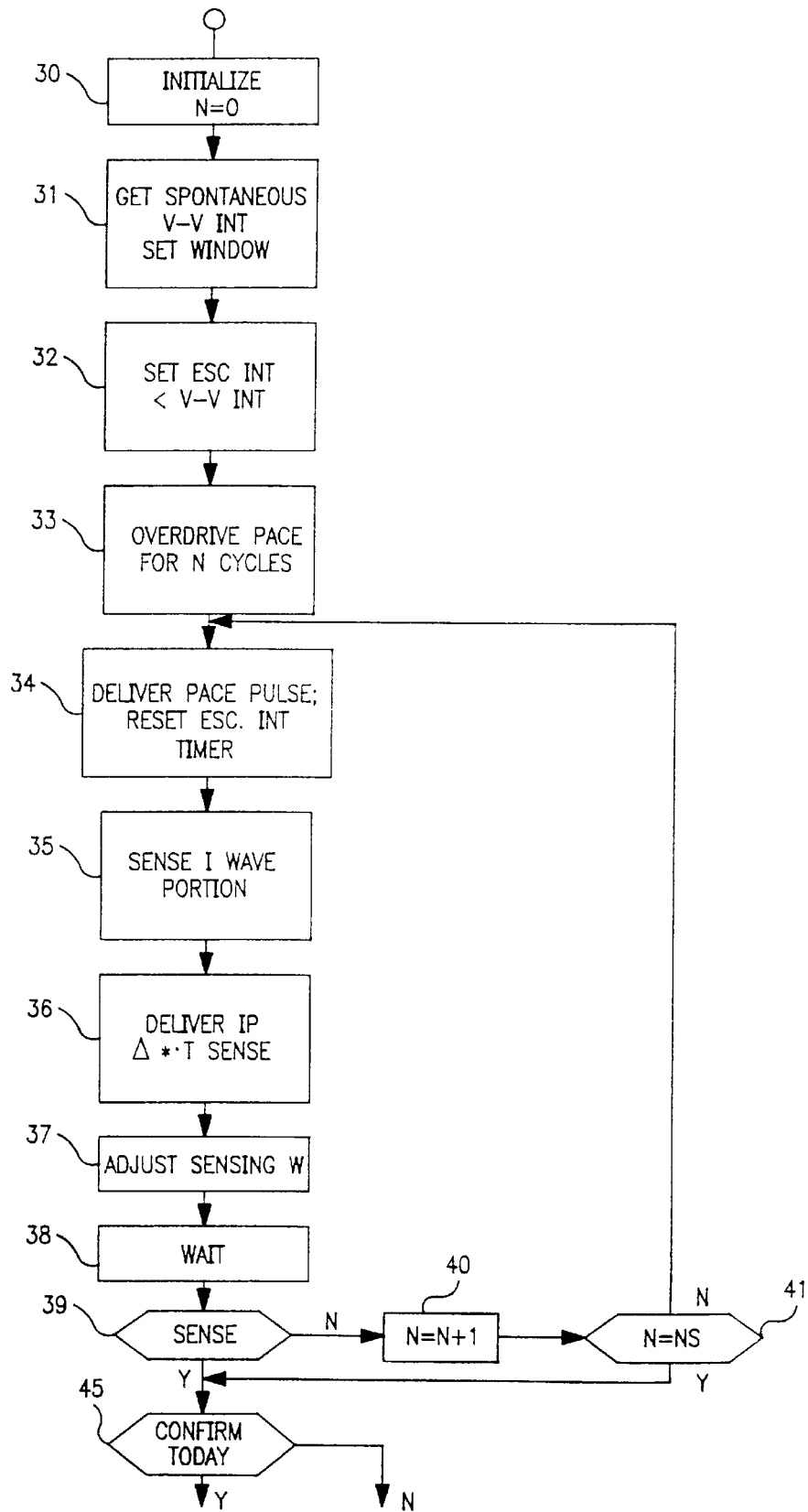
FIG. 3 is a flow diagram illustrating the primary steps taken in accordance with this invention for inducing tachycardia.

Referring now to FIG. 3, there is illustrated a flow diagram representing the primary steps taken in carrying out the routine of this invention for inducing a high rate tachycardia. It is to be understood that the preferred embodiment involves a software routine carried out by the microprocessor 100 and memory 102 or 104, as illustrated in FIG. 1. However, this routine or other equivalent routines can be carried out by other equivalent logic components.

At block 30, the routine is initialized; the number n of initial overdrive pacing pulses is set to a predetermined value, and the number $N_s$ of inducing pulses to be delivered in series is set, e.g., to a value within the range of 1–5, while variable N is set to 0. At 31, the device senses spontaneous heartbeats, and obtains the V—V interval. At 32, the escape interval is set equal to a value less than the V—V interval, so as to overdrive the natural rate. At 33, overdrive pacing pulses are delivered for n cycles, at the overdrive escape interval. Preferably the pulses are tri-phasic, as disclosed in U.S. Pat. No. 4,343,312, in order to minimize polarization. Following this, as indicated at 34, a first pace pulse is delivered, again at the overdrive escape interval which has been set, and the escape interval timer is reset. At 35, the selected T-wave portion, preferably the falling edge, is detected. At 36, the inducing pulse is delivered at a predetermined time relative to the T sense. In a preferred embodiment, the inducing pulse is delivered directly upon detection of the falling edge of the T-wave, although the invention may be practiced by first timing out a short delay, Δt. Detection can be accomplished, e.g., by detecting the peak amplitude and waiting for a very short time corresponding to the downslope; or by differentiating the T-wave signal and detecting when the slope goes negative. After this, the T sense window W is adjusted as shown at 37, i.e., it is shifted forward/backward relative to the stimulus pulse, to track the T-wave. The device then waits, as illustrated at 38. If the waiting is ended by a sense at block 39, this indicates the occurrence of a spontaneous R wave before timeout of the next escape interval, which could indicate that tachycardia has been induced. The routine then branches to 45, and carries out a procedure for confirming tachycardia in accordance with conventional techniques. If, following the wait at 38, there is not a sense at 39, but a timeout of the escape interval, the routine increments N by 1, as indicated at 40; if N is found to be equal to $N_s$ at 41, this indicates the series has been completed, and the routine branches to 45. However, if N is not equal to $N_s$, the routine branches back to 34, and proceeds to deliver the next overdrive pace pulse and following inducing pulse. The routine thus controls the device to deliver a series of inducing pulses, each timed in relation to the T-wave following the last delivered stimulus pulse. If tachycardia is induced before the entire series is delivered, the series is terminated; if following the series, tachycardia has not been induced, a next series can be initiated by an appropriate command from the programmer.

Figure 4A:
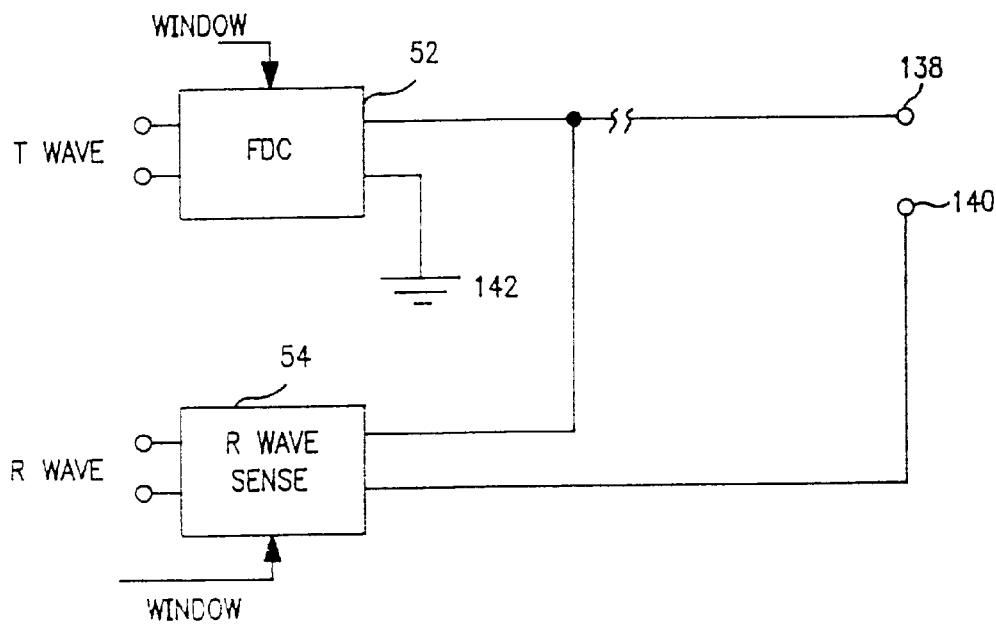
FIG. 4(*a*) is a block diagram illustrating the use of a field density clamp circuit with a unipolar lead, for sensing the T-wave.

As discussed above, the timing of each inducing pulse in the series of delivered inducing pulses is critical, and must be determined accurately with respect to each T-wave. Thus, after the first delivered inducing pulse, the QT interval during the next cycle may be altered due to the effect of the inducing pulse. Further, it is important to position the inducing pulse on the downward slope, or falling edge of the T-wave. These requirements place additional design burdens on the lead electrode characteristics and the sensing circuitry as used for detecting the T-wave. In order to provide optimum detection of the T-wave and timing of the delivery of the inducing pulse, near field sensing is desired. In other words, it is desired to sense as accurately as possible the repolarization of the cells at the location of the tip electrode where the inducing pulse is delivered. This requirement of near field, or localized sensing, can be achieved with particular benefit by using one of the configurations illustrated in FIGS. 4(a), and 4(b). In FIG. 4(a), the input circuit 110 comprises an FDC, or field density clamp circuit 52. The field density clamp circuit is disclosed in U.S. Pat. Nos. 5,156,149 and 5,233, 985, assigned to the same assignee as this invention, both of which patents are incorporated herein by reference. The field density clamp circuit is of advantage in association with a unipolar lead, and is shown having one input connected to ground as illustrated at 142, and the other input connected to tip electrode 138. The FDC circuit acts to essentially clamp the voltage at the tip 138 to that at the indifferent electrode 142, e.g., the pacemaker can. By this technique, a signal is induced by the FDC circuit which is a highly accurate near field signal representative of the changes in the vicinity of electrode 138. Thus, the combination of an FDC input circuit and a unipolar lead provides a desirable near field T-wave signal for use in connection with this invention.

It is to be understood that the use of an FDC circuit as part of this invention does not limit the lead design to being unipolar. Thus, a bipolar lead can be employed, e.g., where electrodes 138 and 140 are used for ventricular pacing and R-wave sensing; and a separate FDC sense channel is used for sensing the T-wave between tip electrode 138 and the indifferent electrode (pacemaker can) 142. As shown in FIG. 4(a), FDC circuit 52 and R-wave sense circuit 54 are separate circuits within block 110 (FIG. 1); each has filter characteristics and/or window enabling for distinguishing the respective signals portions.

Figure 4B:
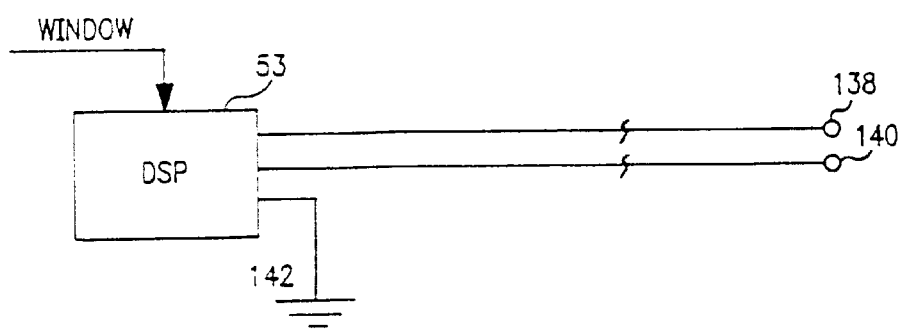

Referring to FIG. 4(b), there is shown an alternate arrangement combining digital signal processing (DSP) circuitry 53 as part of input circuitry 110, with accompanying software, in combination with bipolar sensing from electrodes 138, 140. In this arrangement, ring electrode 140 is suitably close to tip electrode, 138, e.g., less than 10 mm. Such close spacing of the bipolar electrodes yields a sharper near field signal representative of the cell repolarization near the tip electrode 138. For each of the configurations shown in FIGS. 4(a) and 4(b) the T-wave is detected as a very narrow, localized signal, such that it is desirable to trigger generation of the inducing pulse virtually immediately upon sensing of the T-wave downslope, or after a small $\Delta t$ following the T-wave peak.

It is to be noted that the system and method of this invention involve delivery of regular pacing pulses, and thus avoid the need for generating high energy cardioversion or defibrillation-type pulses. Suitably the inducing pulses delivered in accordance with this invention are approximately double the pacing threshold value. For each delivered inducing pulse of the programmed series of pulses, the standard level inducing pulses are delivered in very closely timed relation to cell repolarization in the vicinity of the electrode or electrodes used to deliver the pulses.

We claim:

1. A method of inducing ventricular tachycardia in a patient's heart, comprising:
   stimulating said patient's ventricle with a first pacing pulse to evoke a ventricular contraction;
   measuring a least a portion of the T-wave following said contraction;
   determining the occurrence of a predetermined feature of said T-wave; and
   delivering a second pacing pulse to said patient's ventricle in a predetermined time relationship to said T-wave feature occurrence.

2. The method as described in claim 1, comprising first pacing said patient's ventricle with pacing pulses at an overdrive rate which is greater than the patient's spontaneous rate.

3. The method as described in claim 2, comprising delivering a series of pairs of said first and second pacing pulses until said high rate arrhythmia is induced, each said second pacing pulse being timed with said predetermined time interval relationship to a said occurrence of a said predetermined portion of a said T-wave.

4. The method as described in claim 3, wherein said determining step comprises determining the falling edge of each T-wave.

5. The method as described in claim 1, wherein said determining step comprises determining the falling edge of said T-wave.

6. The method as described in claim 5, wherein said determining step comprises generating an adjustable timing window following the R wave evoked by said first pacing pulse, and sensing said T-wave portion during said window.

7. The method as described in claim 6, comprising adjusting the timing of said window on a cycle-to-cycle basis as a function the position of said falling edge within said window.

8. The method as described in claim 1, wherein said measuring step comprises near field sensing of said T-wave portion at about the site where said pacing pulses are delivered in the patient's ventricle.

9. The method as described in claim 1, wherein said measuring step comprises measuring the patient T-wave across bipolar electrodes positioned in the patient's ventricle.

10. A system for inducing an abnormally high rate in a patient's heart, comprising:
    stimulus pulse means for generating and delivering a series of stimulus pulses at a predetermined rate to a ventricle of said patient,
    sensing means for sensing a predetermined portion of each T-wave which follows each R wave evoked by a said stimulus pulse, and
    inducing means for triggering said stimulus pulse means to generate an inducing pulse following each said sensed predetermined T-wave portion, said inducing means comprising timing means for timing each said inducing pulse in a predetermined time relation to said T-wave portion, whereby a series of inducing pulses are delivered.

11. The system as described in claim 10, further comprising means operative before delivery of said series of stimulus pulses for controlling said stimulus pulse means to generate pacing signals at a rate higher than the patient's spontaneous rate, whereby said stimulus pulse means delivers a series of pacing pulses which overdrive said patient's heart.

12. The system as described in claim 11, wherein said stimulus pulse means comprises series means for generating a series of 1 to 5 pairs of pulses, each said pair comprising a said stimulus pulse and a said inducing pulse.

13. The system as described in claim 11, herein said inducing means comprises means for generating each said inducing pulse immediately upon the sensing of a said T-wave portion.

14. The system as described in claim 10, wherein said inducing means comprises means for generating each said inducing pulse after a predetermined short time delay following the sensing of said T-wave portion.

15. An implantable stimulator system for delivering stimulus pulses to a patient's heart and having the capacity for inducing an abnormally high rate tachycardia in said patient's heart, comprising:
    pulse generator means for generating stimulus pulses and delivering same to at least one chamber of said patient's heart;
    sensing means for sensing patient spontaneous depolarizations in said at least one chamber of said patient's heart;

control means for controlling said pulse generator means to generate and deliver a series of pacing pulses to said at least one chamber at a rate that overdrives said patient spontaneous depolarizations;

repolarization sensing means for sensing repolarizations in said patient chamber following each said delivered pacing pulse; and inducing means responsive to each sensed repolarization for controlling said pulse generator means to generate and deliver an inducing pace pulse to said patient chamber following said each sensed repolarization.

16. The system as described in claim 15, wherein said pulse generator means comprises means for delivering said stimulus pulses to a ventricle of said patient, and said sensing means comprises T-wave means for sensing T-waves from said ventricle.

17. The system as described in claim 16 wherein said pulse generator means comprises a lead with an electrode for delivering pulses to a location of said ventricle, and said repolarization means comprises near field means for obtaining near field signals indicative of repolarizations at about said location.

18. The system as described in claim 16, comprising confirmation means for confirming when a ventricular tachycardia has been induced.

19. The system as described in claim 18, comprising rate means for sensing said patient's spontaneous ventricular rate, and wherein said control means has rate control means for setting the rate of said overdrive pacing pulses just higher than said spontaneous ventricular rate, and said confirmation means has VT means for identifying ventricular tachycardia when a spontaneous ventricular beat is sensed before a said pacing pulse is due to be delivered.

20. The system as described in claim 19, comprising VT means responsive to a spontaneous ventricular beat which is sensed before a next said pacing pulse is due to be delivered, for inhibiting delivery of said next pulse and for identifying an induced ventricular tachycardia.

21. The system as described in claim 15, wherein said control means comprises series means for selecting the number of said overdrive pacing pulses to be delivered in said series.

22. The system as described in claim 21, comprising means operative after said series of overdrive pulses has been delivered for confirming whether ventricular tachycardia has been induced.

23. The system as described in claim 16, wherein said inducing means comprises means for controlling delivery of a said inducing pulse immediately upon sensing of a said T-wave.

24. The system as described in claim 16, wherein said T-wave means comprises feature means for sensing the occurrence of a predetermined feature of a T-wave, and wherein said inducing means comprises interval means for controlling generation and delivery of an inducing pulse at a predetermined interval following said occurrence.

25. The system as described in claim 24, wherein said interval means comprises means for setting said interval to about zero, so that a said inducing pulse is delivered directly upon sensing of said T-wave feature.

26. An implantable pacing system for delivering pacing pulses to a patient's ventricle, having the capacity for inducing a high rate tachycardia in said patient ventricle, comprising.

pulse generator means for generating pacing pulses;

means for delivering said pacing pulses to a location within said patient's ventricle;

depolarization detecting means for detecting spontaneous ventricular depolarizations;

control means for controlling said pulse generator means to generate a series of pacing pulses for delivery to the patient ventricle at a rate that overdrives said ventricular spontaneous depolarizations;

repolarization detection means for detecting near field ventricular repolarization signals near to said ventricular location following each said delivered pacing pulse; and inducing means responsive to each said detected near field repolarization signal for controlling said pulse generator means to generate an inducing pacing pulse for delivery to the patient's ventricle following each said sensed near field repolarization signal.

27. The system as described in claim 26, wherein said control means comprises series means for controlling said pulse generator to generate a said series having 1–n said pacing pulses, where n is a programmable number.

28. The system as described in claim 26, comprising digital signal processing means for processing the signals detected by said repolarization detection means.

* * * * *

UNITED STATES PATENT AND TRADEMARK OFFICE
CERTIFICATE OF CORRECTION

PATENT NO.    : 6,052,621
DATED         : April 18, 2000
INVENTOR(S)   : Begemann et al.

It is certified that error appears in the above-identified patent and that said Letters Patent is hereby corrected as shown below:

Column 8,
Line 49, change "claim 11, herein" to -- claim 11, wherein --.

Signed and Sealed this

Eighteenth Day of March, 2003

JAMES E. ROGAN
*Director of the United States Patent and Trademark Office*